United States Patent [19]

Devault

[11] 4,172,867
[45] Oct. 30, 1979

[54] INDEX PIN AND DIE SPACER COMBINATION FOR DENTAL MODEL

[76] Inventor: Zachary P. Devault, 732 Spring Valley #128, Richardson, Tex. 75080

[21] Appl. No.: 938,463

[22] Filed: Aug. 31, 1978

[51] Int. Cl.$^2$ .......................... A61C 5/10; B29C 1/08
[52] U.S. Cl. .......................................... 264/16; 32/13; 32/17; 164/DIG. 15; 164/34; 164/35; 249/54; 249/62; 264/220; 264/221
[58] Field of Search .................... 264/16–20, 264/219, 220, 221; 32/13–17; 164/DIG. 15, 34, 35; 249/54, 61, 62

[56] References Cited

U.S. PATENT DOCUMENTS

| | | | |
|---|---|---|---|
| 682,098 | 9/1901 | Lyon | 249/54 |
| 1,524,409 | 1/1925 | Simmons | 32/13 |
| 1,857,289 | 5/1932 | Schwartz | 249/54 |
| 2,654,949 | 10/1953 | Whitely et al. | 264/20 |
| 2,705,837 | 4/1955 | Gerlach | 32/13 |
| 2,916,766 | 12/1959 | Barbanotti | 249/54 |
| 3,226,827 | 1/1966 | Spalten | 249/54 |
| 3,461,560 | 8/1969 | Hana | 32/17 |
| 3,469,316 | 9/1969 | Stern et al. | 32/17 |
| 3,570,126 | 3/1971 | Reynaud | 32/17 |

FOREIGN PATENT DOCUMENTS

| | | | |
|---|---|---|---|
| 639401 | 11/1966 | Belgium | 264/19 |
| 26718 | 9/1920 | Denmark | 264/19 |

Primary Examiner—W. E. Hoag
Attorney, Agent, or Firm—Dennis T. Griggs

[57] ABSTRACT

Method and apparatus for preparing a wax replica of a dental prosthesis is disclosed. The method of the invention is carried out by preparing a composite dental model which includes a base portion, an odontal die projecting from the base portion having a cavity in which the dental prosthesis is to be implanted, and an index pin embedded within the composite dental model. A complementary dental model having an odontal projection defining an occlusal surface for engaging the odontal die is also prepared. The index pin includes an anchor shank portion embedded within the odontal die, an alignment shank portion embedded in the base portion and a radially projecting collar portion disposed in the interface of the base portion and the odontal die. The odontal die and embedded index pin are removed from the base portion of the composite dental model and a die spacer is placed around the alignment shank portion of the index pin. After the odontal die together with the die spacer and index pin are reinserted into the base portion of the composite model, a quantity of wax is deposited into the odontal die cavity. The wax deposit is compressed by bringing the occlusal surface of the complementary model into engagement with the occlusal surface of the composite model. The die spacer produces dimensional compensation for the expansion of a gold alloy casting when the wax deposit is used in a conventional investment casting procedure.

2 Claims, 12 Drawing Figures

INDEX PIN AND DIE SPACER COMBINATION FOR DENTAL MODEL

BACKGROUND OF THE INVENTION

1. Field of the Invention

The invention relates generally to restorative dental technology, and in particular to method and apparatus for preparing a wax replica of a dental restoration.

2. Description of the Prior Art

Modern dental practice involves a variety of casting operations, ranging from the simplist inlay to all forms of cast crowns, bridge structures and removable partial dentures, each of which makes use of the same fundamental practices in forming the cast restoration. The structures produced by casting operations represent an important part of restorative dentistry.

In dentistry, the casting procedure is known as the "lost wax technic". Basically, this method consists of forming a wax pattern, surrounding it with investment material, and later heating the investment mold to remove the wax before casting melted metal into the mold. In all instances, regardless of the technic employed or the type of restoration to be cast, it is necessary first to prepare in wax an exact duplicate of the finished restoration. When the formation of an acceptable wax pattern is accomplished, it is surrounded with dental investment, after which investment is permitted to harden to form the mold into which a dental alloy is cast.

When the investment mold has been formed and the wax eliminated by heating, it is then ready to receive the molten metal to form the casting. Proper and careful heating of the investment mold is necessary in order to provide complete wax elimination from the mold. All conventional investment materials display some setting expansion and hygroscopic expansion upon hardening and thermal expansion when they are heated to eliminate the wax from the mold or when they are heated to more elevated temperatures associated with the casting procedure. Because the purpose of the metal casting is to provide a metallic duplication of missing tooth structure with as great an accuracy as possible, it is essential to minimize the expansion associated with investment casing.

The factor of expansion in addition to other factors such as flow and warpage is important in the preparation of a wax pattern which will serve to produce an accurate gold casting. The two most commonplace methods of preparing a wax pattern are the "direct" and "indirect" technics. The method of preparing a wax pattern is called "direct" if the wax pattern is prepared in the patient's mouth. On the other hand, if an impression is taken from the cavity preparation and a die is formed from the impression on which the pattern is prepared, then the method is called "indirect".

When a wax pattern is formed by the indirect method, a dental stone die is used which is the positive replica of at least a portion of the surrounding tooth structure and the cavity preparation. This tooth replica permits the pattern to be formed outside of the mouth. A cavity for receiving a gold crown is typically prepared by cutting away surrounding portions of the tooth to form horizontal and vertical surfaces. Because of this special cavity preparation, the lateral dimensions of the gold crown can be adjusted relatively easily in the laboratory to insure a good fit. However, vertical expansion of the gold crown is extremely difficult to correct because of the complex shape of the occlusal surface. According to conventional corrective procedures, correction is carried out by grinding and polishing after the crown has been secured to the prepared cavity in the patient's mouth. A good occlusion fit is very difficult to obtain by this procedure because of the complex contour of the occlusion surface and because of limited access when working in the patient's mouth. Therefore it would be desirable to provide method and apparatus for compensating for the thermal expansion of the gold casting and thereby minimize the amount of "touch up" dental work required to provide a good occlusal fit.

SUMMARY OF THE INVENTION

It is a principal object of the present invention to provide method and apparatus for preparing a wax replica of a dental restoration such as a metallic crown which compensates for dimensional expansion of the crown associated with conventional investment casting.

It is an important object of the present invention to provide an index pin which can be imbedded within a composite dental model of the type used to prepare a dental prosthesis which will permit an odontal die in which it is embedded to be removed from the composite model and reinserted in alignment with a complementary occlusal surface.

Yet another object of the invention is the provision of an index pin which makes possible the removal of an odontal die from a composite dental model and reinsertion of the odontal die and index pin into the composite dental model together with a die spacer which displaces the die to compensate for the thermal expansion associated with an investment casting procedure which utilizes a wax replica prepared by the composite model.

The foregoing objects are achieved by means of an index pin embedded within a composite dental model having an odontal die disposed for engagement with an occlusal surface of a complementary dental model. The index pin comprises an anchor shank portion embedded within the odontal die, an alignment shank portion embedded within the base portion of the composite model and a radially projecting collar disposed intermediate the anchor shank and the alignment shank. The collar includes a planar surface disposed substantially flush with the interface surface of the odontal die. A die spacer is removably disposed intermediate the collar and the interface surface of the dental model base portion for displacing the die radially with respect to its natural elevation in the model.

A wax replica of a dental restoration is produced by preparing a dental model having an odontal projection defining an occlusal surface for engaging an odontal die having a cavity in which a dental prosthesis is to be implanted. A composite dental model is also prepared which includes a base portion, an odontal die projecting from the base portion and having a cavity in which the dental prosthesis is to be implanted and an index pin having an anchor shank portion embedded in the odontal die, an alignment shank portion embedded in the base portion and a radially projecting collar disposed in the interface of the base portion and odontal die. Thereafter, the odontal die together with the embedded index pin is removed from the base portion of the composite dental model. A die spacer is placed around the alignment shaft intermediate the interface surface of the collar and the interface surface of the base portion of the composite model to produce the desired displacement. The odontal die together with the embedded index pin and die spacer are inserted into the composite model by placing the alignment shank of the imbedded index pin into the alignment shank cavity. A quantity of wax is deposited into the odontal die cavity and is compressed by engaging the wax deposit and die with the complementary occlusal surface of the odontal projection. Thereafter, the occlusal surface is withdrawn and the compressed wax deposit is removed from the odontal die cavity. After conventional wax sculpturing procedures, the compressed wax deposit is embedded within a conventional investment mold and is removed by melting prior to casting melted metal into the mold to produce the dental prosthesis.

The novel features which characterize the invention are defined by the appended claims. The foregoing and other objects, advantages and features of the invention will hereinafter appear, and for purposes of illustration, but not of limitation, an exemplary embodiment of the index pin apparatus of the invention and of a dental model with which the method of the invention may be practiced is shown in the appended drawings.

DETAILED DESCRIPTION OF A PREFERRED EMBODIMENT

Figure 1:
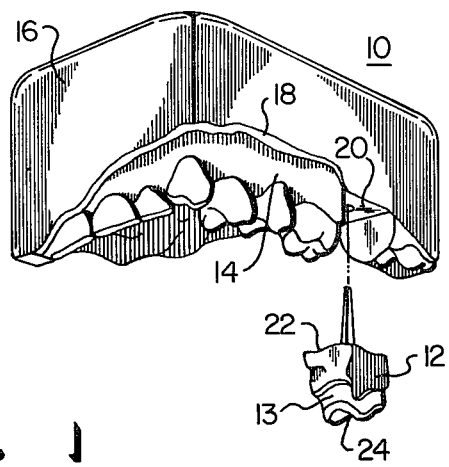
FIG. 1 is a perspective view of a composite dental model constructed according to the teachings of the present invention.

For purposes of illustration, the invention will be explained with reference to the preparation of a wax pattern for a gold crown. However, the method and apparatus of the invention may be utilized to produce other dental prostheses such as simple inlays, onlays, denture bases, bridge structures and removable partial dentures typically used in restorative dentistry.

In the description which follows, like parts are marked throughout the specification and drawing with the same reference numerals, respectively. The drawing figures are not necessarily to scale and in some instances portions have been exaggerated in order to more clearly depict certain features of the invention.

Referring now to FIG. 1, a composite dental model 10 including an odontal die 12 is illustrated. The composite dental model 10 is formed by first pouring a quantity of dental stone into an impression provided by a dentist to produce a positive replica 14 of the tooth structure and gum formation. A layer of dental stone or some other suitable composition is then poured over the top of the positive replica 14 to provide a base 16 to facilitate handling. The interface of the positive replica 14 with the base portion 16 is identified by the line 18. The material forming the base portion 16 is preferably different from the material forming the positive replica 14 so that the odontal die 12 can be easily broken away to leave a smooth interface surface 20 on the base portion 16 and a corresponding smooth interface surface 22 on the odontal die 12.

The occlusal surface of the odontal die 12 is erroded by a cavity 24 which has been enlarged and finished with vertical and horizontal planar surfaces (FIG. 11) according to conventional dental practice. The prepared cavity 24 is restored with a gold crown instead of a cement filling because of the extensive nature of the restoration required and because there is insufficient tooth structure remaining to support a conventional cement filling.

The first step in the preparation of a gold crown is the preparation of a wax pattern. The wax pattern should be an accurate reproduction of the missing tooth structure. The wax pattern forms the outline of the mold into which gold alloy is cast. Because the casting can be no more accurate than the wax pattern, the wax pattern should be well adapted to the prepared cavity, properly carved, with minimum distortion. After the pattern has been removed from the prepared cavity 24, it is surrounded by a gypsum investment material in an investment mold. After the investment is permitted to harden, the mold is heated to remove the wax before casting the melted alloy.

According to the prior art, the wax pattern is produced by depositing a quantity of wax in the cavity 24 and then compressing the wax within the cavity by engaging the occlusal surface of the odontal die 12 with the corresponding occlusal surface of a second dental model representative of the teeth in the lower or upper jaw which corresponds in position with the tooth being restored. Thereafter, the die 12 is removed and the compressed wax deposit is carved and finished to provide an acceptable gingival interface. However, post-casting adjustment of the crown occlusal surface is carried out after the crown has been seated in the tooth which is being restored. As previously discussed the adjustment of the radial projection of the occlusal surface to produce an acceptable bite requires a great deal of skill and artistic ability because of the complex curvature of the occlusion.

Absolute accuracy of fit cannot be realized continuously under oral conditions because of the differential thermal dimensional changes between the tooth and the gold crown and other factors. However, the more accurate fit of the crown in the prepared cavity, the less is the likelihood of leakage and the occurrence of caries. Because the lateral dimensions of the gold crown are relatively easy to adjust owing to the planar surface configuration of the prepared cavity 24, further accuracy can be obtained by controlling or compensating in some way for the radial expansion or enlargement of the gold crown during the investment casting. This is carried out in the present invention by embedding an index pin 28 (FIG. 8) into the composite dental model 10 which will permit the odontal die 12 to be cut away and removed from the positive replica 14 along the interface 18 between the base portion 16 and positive replica 14. The presence of the index pin 28 in the odontal die 12 insures that it will be accurately aligned in its original position when the die is returned to the model.

Figure 3:
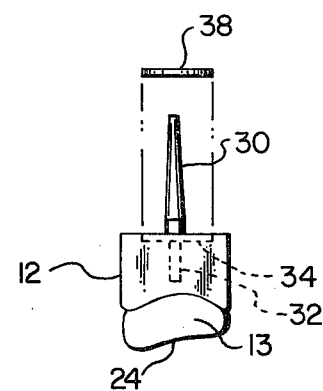
FIG. 3 is a side view, in elevation, of the odontal die shown in FIGS. 1 and 2 which illustrates the coupling engagement of a die spacer with the alignment shank of an index pin constructed according to the teachings of the present invention.
Figure 4:
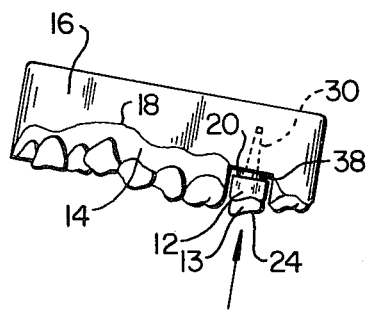
FIG. 4 is a side view, in elevation, of the composite dental model shown in FIG. 2 and including the index pin and die spacer combination shown in FIG. 3.
Figure 8:
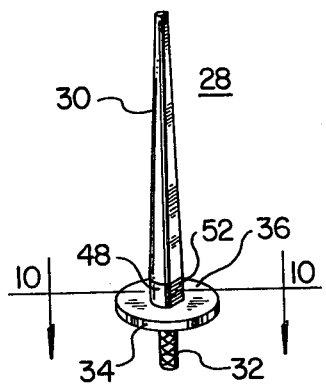
FIG. 8 is a perspective view of a preferred embodiment for an index pin constructed according to the teachings of the present invention.
Figure 9:
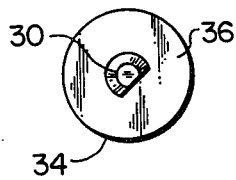
FIG. 9 is a top plan view of the index pin shown in FIG. 8.
Figure 12:
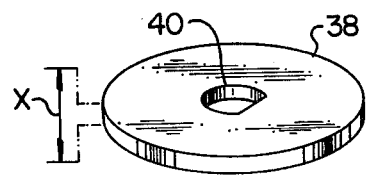
FIG. 12 is a perspective view of the die spacer shown in FIGS. 3 and 11.

Referring now to FIG. 8, the index pin 28 comprises an anchor shank portion 30 which is embedded within the die 12, an alignment shank portion 32 which is embedded within the base portion 16 and a radially projecting flange or collar 34 disposed intermediate the anchor shank 30 and alignment shank 32. The flange or collar 34 is preferably in the form of an annular disc; however, other curved arrangements such as oval or elliptical and polygonal forms such as square, rectangular or triangular may be used to good advantage. The flange or collar 34 is preferably formed in a continuous piece; however, a flange 34 having articulated edge portions may be used to good advantage. The collar 34 has a substantially planar surface 36 disposed orthogonally with respect to the longitudinal axis of the anchor shank 32. The purpose of the planar surface 36 is to form a smooth platform on the interface surface 20 of the base portion 14 for engaging and retaining the planar side surface of a die spacer 38 as shown in FIGS. 3 and 12.

The die spacer 38 is preferably a circular disc having an opening 40 for receiving the alignment shank portion 32 of the index pin 28. The thickness of the die spacer 38 is indicated by the letter X in FIG. 12 and is typically 0.1 millimeter to 0.2 millimeter. This dimension corresponds to the expected radial expansion of the metallic crown material relative to the wax pattern during the investment casting procedure. Experience has shown that a gold alloy crown undergoes expansion approximately equal to 2% of the original dimension of the wax pattern. The expansion of the gold crown is generally proportional to the volume of gold comprising the crown.

Figure 5:
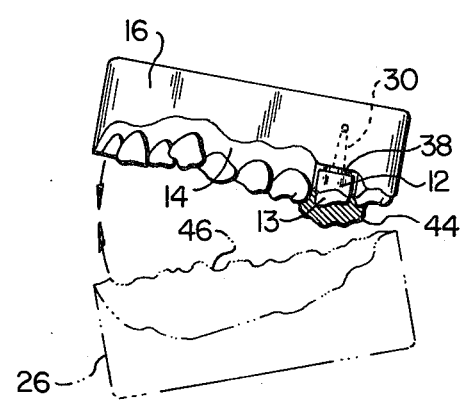
FIG. 5 is a side view, in elevation, of the composite dental model shown in FIG. 1 in combination with a complementary dental model for compressing a wax deposit within an odontal die cavity.
Figure 6:
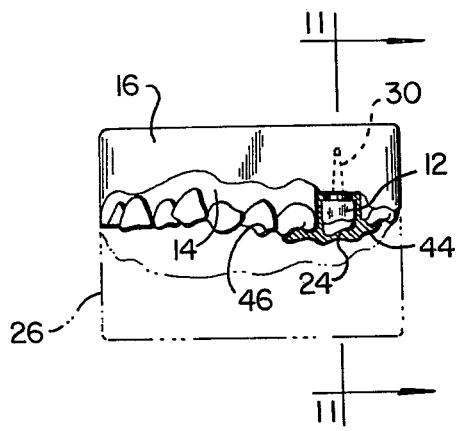
FIG. 6 is a view similar to FIG. 5 which illustrates the occlusal engagement of the composite dental model and complementary model shown in FIG. 5.
Figure 7:
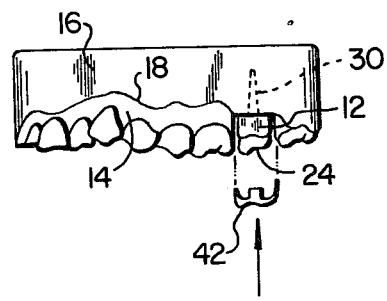
FIG. 7 is a side view, in elevation, which illustrates the removal of the compressed wax deposit from a die cavity.
Figure 11:
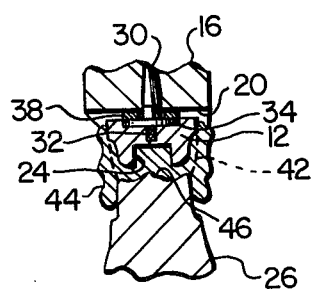
FIG. 11 is a sectional view taken along the lines 11—11 of FIG. 6.

The purpose of the die spacer 38 is, therefore, to displace or radially offset the die 12 with respect to the interface surface 20 of the interface 18. This displacement minimizes the radial thickness of a wax pattern 42 which is formed when a wax deposit 44 disposed within the cavity 24 is compressed. Referring now to FIGS. 5, 6 and 11, the wax deposit 44 is compressed to form the wax pattern 42 by engaging the wax deposit 44 and die 12 with the occlusal surface 46 of the opposing dental model 26. Thereafter, the die 12 together with the wax deposit 44 is removed from the base portion 16 and the wax is sculptured to define an acceptable inlay-gingival boundary. The sculptured wax pattern 42 is then attached to a suitable spru, inserted into a mold and surrounded by an investment casting. After the investment has hardened and the wax pattern has been withdrawn by melting, a gold alloy is shot into the mold cavity in a centrifugal casting machine. After casting, the crown is bonded by cement or is otherwise implanted in the prepared cavity as a restoration of the decayed or damaged tooth.

Figure 2:
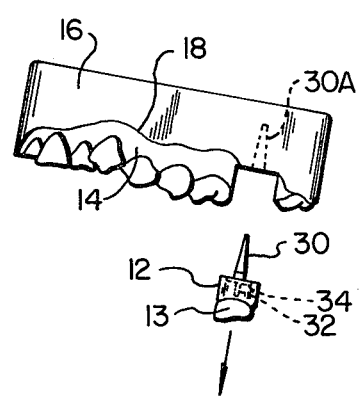
FIG. 2 is a side elevation view of the dental model of FIG. 1, partly broken away, to illustrate removal of an odontal die.
Figure 10:
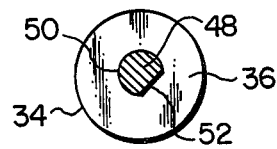
FIG. 10 is a sectional view taken along the lines 10—10 of FIG. 8.

To maintain the exact orientation of the odontal die 12, the alignment shank 30 of the index pin 28 preferably comprises an intermediate portion 48 having a constant cross-section. As can be seen in FIGS. 8 and 10, the constant cross-section of the intermediate section 48 is formed by the intersection of a cylindrical side surface 50 and a planar side surface 52. The intermediate portion 48 may also be formed by three or more intersecting planar surfaces. The purpose of the constant cross-section intermediate portion 48 is to permit the alignment shank portion 30 to be displaced slightly from its cavity 30A (FIG. 2) without twisting or tilting with respect to the radial axis of the cavity 30A.

Angular orientation is maintained by providing the intermediate portion 48 with at least one planar surface, for example the surface 52. The intersection of the planar surface 52 with the cylindrical surface 50 prevents rotation of the alignment shank portion 30 within its cavity 30A.

As can best be seen in FIG. 8, the alignment shank 30 of the index pin 28 is preferably tapered. Also, the anchor shank portion 32 is preferably serrated to strengthen its embedded engagement within the die 12. In the preferred embodiment shown in FIG. 8, the alignment shank portion is tapered and is formed by a conical side surface and a planar side surface. However, other alignment shank configurations which may be easier to manufacture may be used to good advantage.

The index pin 28 is preferably stamped from a ductile material such as aluminum or brass and the die spacer 12 is preferably nylon or a metal such as aluminum. The wax deposit 44 is preferably Type II as identified by the American Dental Association Specification Number 4 for indirect technics. The positive replica 14 is preferably formed of Class II dental stone powder mixed with water or some suitable gypsum hardener solution.

From the foregoing description of preferred embodiments of the invention, those skilled in the art will appreciate that the present invention provides method and apparatus for preparing a wax pattern for use in investment casting procedures which minimizes the effect of the expansion of the alloy casting. Although preferred embodiments of the invention have been described in detail, it should be understood that various changes and alterations can be made therein without departing from the spirit and scope of the invention as defined by the appended claims.

What is claimed is:

1. A method for prepairng a wax replica of a dental restoration comprising the steps:
   preparing a dental model having an odontal projection defining an occlusal surface which is complementary to the occlusal surface of an odontal die having a cavity in which a dental prosthesis is to be implanted;
   preparing a composite dental model including a base portion, an odontal die projecting from the base portion and having a cavity in which a dental prosthesis is to be implanted, and an index pin having an anchor shank portion embedded within the odontal die, an alignment shank portion embedded within the base portion and a radially projecting collar disposed in the interface of the base portion and odontal die;

removing the odontal die together with the embedded index pin from the base portion of the composite dental model;

placing a die spacer intermediate the interface surface of the collar and the interface surface of the base portion and returning the odontal die to the composite model by inserting the alignment shank of the embedded index pin into the alignment shank cavity;

depositing a quantity of wax into the odontal die cavity;

compressing the wax deposit by engaging the wax deposit and die with the complementary occlusal surface of the odontal projection; and withdrawing the complementary occlusal surface and removing the compressed wax deposit from the odontal die cavity.

2. Apparatus for preparing a wax replica of a dental restoration comprising, in combination:

a first dental model having an occlusal surface;

a second dental model including a base portion and an odontal die removably secured to said base portion and projecting from the base portion for complementary engagement with the occlusal surface of the first dental model, the odontal die having a cavity for receiving a wax deposit;

an index pin having an alignment shank removably disposed within the base portion, an anchor shank embedded within the odontal die and a radially projecting collar disposed intermediate the alignment shank and anchor shank, said collar having a planar surface disposed substantially flush with the interface surface of the odontal die; and a die spacer removably disposed intermediate said collar and the interface surface of said dental model base portion.

* * * * *

UNITED STATES PATENT AND TRADEMARK OFFICE
CERTIFICATE OF CORRECTION

PATENT NO. : 4,172,867
DATED : October 30, 1979
INVENTOR(S) : Zachary Paul Davault It is certified that error appears in the above—identified patent and that said Letters Patent is hereby corrected as shown below:

Inventor's name "Devault" should read -- Davault --.

Signed and Sealed this

Nineteenth Day of February 1980

[SEAL]

Attest:

SIDNEY A. DIAMOND

Attesting Officer     Commissioner of Patents and Trademarks